United States Patent
Shroot et al.

Patent Number: 5,153,212
Date of Patent: Oct. 6, 1992

[54] 2-ADAMANTYL-4-ISOTHIAZOLINE-3-ONES, AS BACTERICIDAL AND FUNGICIDAL AGENTS

[75] Inventors: Braham Shroot, Antibes; Jean Maignan, Tremblay Les Gonesse; Rainer Schmidt, Mougins, all of France

[73] Assignee: Centre International De Recherches Dermatologiques (C.I.R.D.), Valbonne, France

[21] Appl. No.: 709,227

[22] Filed: Jun. 3, 1991

Related U.S. Application Data

[63] Continuation of Ser. No. 544,874, Jun. 28, 1990, abandoned, which is a continuation of Ser. No. 348,911, May 8, 1989, abandoned.

[30] Foreign Application Priority Data

May 9, 1988 [FR] France .................. 88 06222

[51] Int. Cl.$^5$ .................. A01N 43/78; C07D 275/03
[52] U.S. Cl. .................. 514/372; 546/114; 546/291; 548/209; 548/213; 564/189; 564/191
[58] Field of Search .................. 548/213; 514/372

[56] References Cited

U.S. PATENT DOCUMENTS

| | | | |
|---|---|---|---|
| 3,706,758 | 12/1972 | Grivas | 548/209 |
| 3,932,487 | 1/1976 | Kramer et al. | 564/189 |
| 4,127,687 | 11/1978 | Dupont | 514/372 |
| 4,243,403 | 1/1981 | Lewis et al. | 514/372 |

FOREIGN PATENT DOCUMENTS 2087388 5/1982 United Kingdom .

OTHER PUBLICATIONS

French Search Report of FR8806222.

Primary Examiner—Mukund J. Shah
Assistant Examiner—Philip I. Datlow
Attorney, Agent, or Firm—Cushman, Darby & Cushman

[57] ABSTRACT

2-adamantyl-4-isothiazoline-3-one has the formula

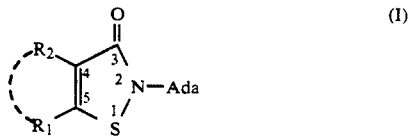

wherein
$R_1$ and $R_2$, each independently, represent hydrogen or halogen,
or $R_1$ and $R_2$, taken together, form a polymethylene chain having 3-4 carbon atoms, optionally substituted by lower alkyl or halogen,
or $R_1$ and $R_2$, taken together, form a pyridine ring with the double bond of the 4-isothiazoline-3-one ring and
Ada represents 1'-adamantyl, 2'-adamantyl or 1'-adamantyl methyl, and its mineral or organic acid salt.
The compound is useful as an antibacteria, antialgae or antifungus agent in various industrial fields.

8 Claims, No Drawings

2-ADAMANTYL-4-ISOTHIAZOLINE-3-ONES, AS BACTERICIDAL AND FUNGICIDAL AGENTS

This application is continuation of application Ser. No. 07/544,874 filed Jun. 28, 1990, now abandoned, which is a continuation of application Ser. No. 07/348,911 filed May 8, 1989, now abandoned.

The present invention relates to new 4-isothiazoline-3-one derivatives, and more particularly to 2-adamantyl-4-isothiazoline-3-ones, to a process for their preparation and to their use as bactericidal and fungicidal agents.

In French Patent No. 80.22278 (2.492.376), there has already been proposed 4,5-polymethylene-4-isothiazoline-3-ones of the general formula

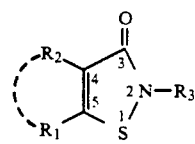

wherein $R_1$ and $R_2$, taken together form a polymethylene chain having 3-4 carbon atoms or a polymethylene chain having 3-4 carbon atoms substituted by a lower alkyl radical having 1-4 carbon atoms, and $R_3$ is capable of representing various radicals, and principally a cycloalkyl radical having 3-6 carbon atoms.

Studies carried out on these 4-isothiazoline-3-ones, substituted in the 2-position by a cycloalkyl radical, have evidenced that these compounds are active effectively with respect to bacteria, but that their activity is, however, inferior to that of derivatives substituted in the 2-position by linear or branched alkyl having 1-4 carbon atoms.

As a result of new studies, it has now surprisingly been found that 4-isothiazoline-3-ones, substituted in the 2-position by an adamantyl radical, exhibit excellent bactericide and fungicide activity and that they are less toxic to mammals.

It has been particularly noted that these new derivatives, substituted in the 2-position by an adamantyl radical, are particularly powerful antifungus agents.

The present invention thus relates to 2-adamantyl-4-isothiazoline-3-ones which can be represented by the following general formula:

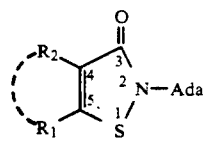

wherein $R_1$ and $R_2$, each independently, represent hydrogen or halogen, or $R_1$ and $R_2$, taken together, form a polymethylene chain having 3 or 4 carbon atoms, optionally substituted by lower alkyl or halogen, $R_1$ and $R_2$, taken together, form a pyridine ring with the double bond of the 4-isothiazoline-3-one ring, and Ada represents an adamantyl radical selected from the group consisting of

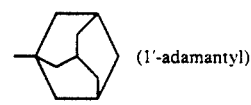

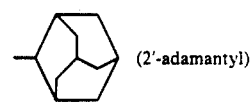

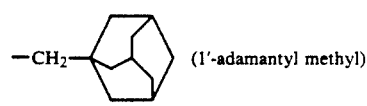

and their salts of a mineral or organic acid.

The halogen of the $R_1$ and $R_2$ radicals is preferably fluorine, bromine or chlorine.

When the $R_1$ and $R_2$ radicals, taken together, form a pyridine ring with the double bond of the 4-isothiazoline-3-one, the pyridine ring can be substituted by one or more lower alkyls having 1-4 carbon atoms or by at least one halogen such as fluorine, chlorine or bromine, or even by a nitro radical.

In accordance with a first embodiment of the present invention, the 2-adamantyl-4-isothiazoline-3-ones can be represented by the general formula:

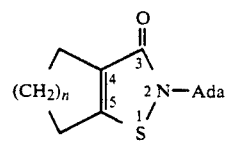

wherein

Ada has the same meaning given in formula (I) and n is 1 or 2.

It is a question then of 2-adamantyl-4-5-trimethylene or tetramethylene-4-isothiazoline-3-ones.

In accordance with a second embodiment of the present invention, the 2-adamantyl-4-isothiazoline-3-ones can be represented by the following general formula:

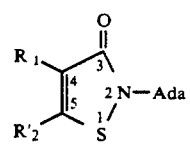

wherein

Ada has the same meaning given for formula (I), and $R'_1$ and $R'_2$, each independently, represent hydrogen or halogen such as fluorine, chlorine or bromine.

In accordance with this second embodiment, Ada is preferably 1'-adamantyl or 2'-adamantyl.

Finally, in accordance with a third embodiment of the present invention, the 2-adamantyl-4-isothiazoline-3-ones can be represented by the following general formula:

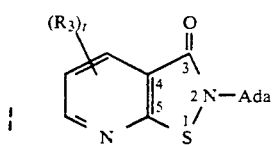

wherein

Ada has the same meaning as that given for formula (I),

R₃ represent hydrogen, lower alkyl having 1-4 carbon atoms, fluorine, chlorine, bromine or nitro, and t is 1 or 2.

It is a question then of 2-adamantyl-(5,4b) isothiazolo-3-pyridinones, optionally substituted.

When the compounds in accordance with the present invention are provided in the form of salts of a mineral or organic acid it is a question more particularly of hydrochlorides, hydrobromides, nitrates, sulfates or succinates.

The particularly preferred 2-adamantyl-4-isothiazoline-3-ones, in accordance with the present invention, are those represented by general formula (III) in which the Ada radical represents 1'-adamantyl or 2'-adamantyl and R'₁ and R'₂ represent hydrogen or chlorine, at least one of R'₁ or R'₂ representing chlorine.

Representative compounds, in accordance with the present invention, which correspond to formulas (I) to (IV) include, in particular, the following:

2-(1'-adamantyl)-4,5-trimethylene-4-isothiazoline-3-one, 2-(1'-adamantyl methyl)-4,5-trimethylene-4-isothiazoline-3-one, 2-(2'-adamantyl)-4,5-trimethylene-4-isothiazoline-3-one, 2-(2'-adamantyl)-(5,4b)-isothiazolo-3-pyridinone, 2-(2'-adamantyl)-4-isothiazoline-3-one, 2-(2'-adamantyl)-5-chloro-4-isothiazoline-3-one, 2-(2'-adamantyl)-4,5-dichloro-4-isothiazoline-3-one, 2-(1'-adamantyl)-4-isothiazoline-3-one, 2-(1'-adamantyl)-5-chloro-4-isothiazoline-3-one, 2-(1'-adamantyl)-4,5-dichloro-4-isothiazoline-3-one, 2-(1'-adamantyl)-5-bromo-4-isothiazoline-3-one, 2-(1'-adamantyl)-4-bromo-5-chloro-4-isothiazoline-3-one, and 2-(2'-adamantyl)-4-bromo-5-chloro-4-isothiazoline-3-one.

The compounds in accordance with the present invention can be prepared by various processes, and principally by the process described by Goerdeler and Mittler, Chem. Ber. 96, 944-954 (1963), which consists in cyclizing in an inert organic solvent a 2-carbamoyl thiocyclanone (1) in accordance with the following reaction scheme:

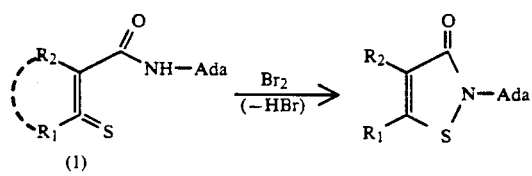

For the preparation of 2-adamantyl-4,5-polymethylene-4-isothiazoline-3-ones, it is preferred however to use the process described in French Patent No. 85.08469 (2.583.046).

This process can also be advantageously employed for the preparation of 2-adamantyl-(5,4b)-isothiazolo-3-pyridinones.

This process can be represented by the following reaction scheme:

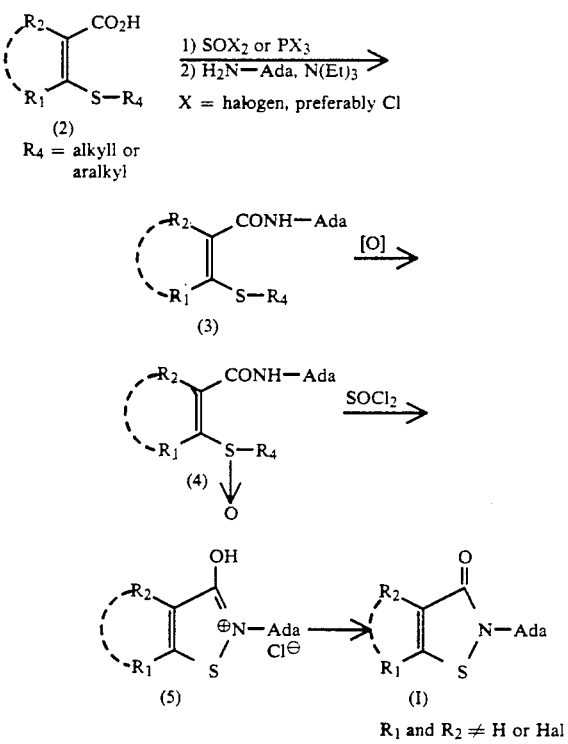

R₁ and R₂ ≠ H or Hal

The first step of this process consists in preparing a 2-alkyl or aralkyl thiocarboxamide (3) starting with a 2-alkyl or aralkyl thiocarboxylic acid (2) by transforming it into the acid chloride by treatment with thionyl chloride or a phosphorus trihalide (preferably phosphorus trichloride) in an aromatic solvent such as toluene or a chlorinated solvent such as 1,2-dichloroethane or methylene chloride. The intermediate acid chloride is then transformed into the 2-alkyl or aralkyl thio carboxamide (3) by reacting it with an adamantylamine (H₂N-Ada) in the presence of triethylamine.

The sulfoxides (4) of the compounds of formula (3) are obtained by the action either of m-chloroperbenzoic acid or by the action of an organic peracid formed in situ by the addition of H₂O₂ to an organic acid such as formic acid or acetic acid. This reaction is effected by dissolving the 2-alkyl or aralkyl thio carboxamide (3) in this pure organic acid or by mixing it with a chlorinated solvent such as methylene chloride, then slowly adding at 0° C. the H₂O₂. After the end of the addition, the mixture is then stirred for 1-2 hours at ambient temperature and there is obtained, in a very good yield, the corresponding sulfoxide derivative (4) which is purified in accordance with conventional procedures.

The cyclization reactions of the sulfoxides (4), with the view of obtaining the hydrochlorides of the 2-adamantyl-4-isothiazoline-3-ones of formula (5), is preferably carried out in the organic solvent such as, for example, methylene chloride in the presence of an acid chloride such as thionyl chloride.

The cyclization reaction is very selective and the expected hydrochlorides precipitate in the reaction mixture. However, when they are soluble they can be easily precipitated by the addition of isopropyl ether.

The hydrochlorides of the 2-adamantyl-4-isothiazoline-3-ones (5) are particularly lipophilic. It is very easy to transform them into a free base simply by washing with water in a solution or suspension of the hydrochloride in an organic solvent such as toluene, dichloromethane or even methylene chloride. Generally, after the third washing with water, the aqueous phase no longer contains chloride ions.

The starting products of this process for preparing the compounds according to the present invention are (i) 2-polymethylene alkyl or aralkyl thio carboxylic acids and (ii) 2-alkyl or aralkyl thio nicotinic acids.

The preparation of 2-polymethylene alkyl or aralkyl thio carboxylic acids is described in French Patent No. 85.08469 (2.583.046).

The 2-alkyl or aralkyl thio nicotinic acids are obtained starting with 2-chloronicotinic acid by displacement reaction of the chloride by a potassium or sodium thiolate, prepared starting with an alkyl or aralkyl mercaptan of the formula $R_4SH$.

The compounds according to the invention of general formula (I), wherein $R_1$ and/or $R_2$ represent hydrogen or halogen, are preferably obtained starting with 3-mercapto propionamide derivatives in accordance with the method described by S. N. Lewis et al., J. Heter. Chem. 571, 1971.

This process can be represented by the following reaction scheme:

produce the 2-adamantyl-4-isothiazoline-3-ones in accordance with two synthesis methods.

In accordance with the first method, the N-adamantyl-3-acetylthio propionamide (8) is transformed into the corresponding thiol (9) by treatment in methanol in an acid medium. The latter is then oxidized in the presence of $H_2O_2$ into the corresponding disulfide (10). By reaction with a halogen, the disulfide (10) is transformed into 2-adamantyl-4-isothiazoline-3-one. Following the amounts of halogen employed, one can direct the formation either to non-halogenated and mono-halogenated 4-isothiazoline-3-one or to 4,5-mono- and dihalogeno-4-isothiazoline-3-ones.

In accordance with the second method, sulfuryl chloride is reacted directly with the N-adamantyl-3-acetylthio propionamide (8) dissolved in toluene. There is thus obtained, as the preponderant product, 2-adamantyl-5-chloro-4-isothiazoline-3-one (11).

The present invention also relates to this second method for the synthesis of 2-adamantyl-4-isothiazoline-3-ones, mono-halogenated in the 5-position, this being particularly advantageous because it avoids the preparation of the thiol (9) and its disulfate (10) and moreover the mono-halogenation of the double bond is more selective.

The present invention also relates to, as new industrial products, intermediate synthesis compounds having the following formula (V)

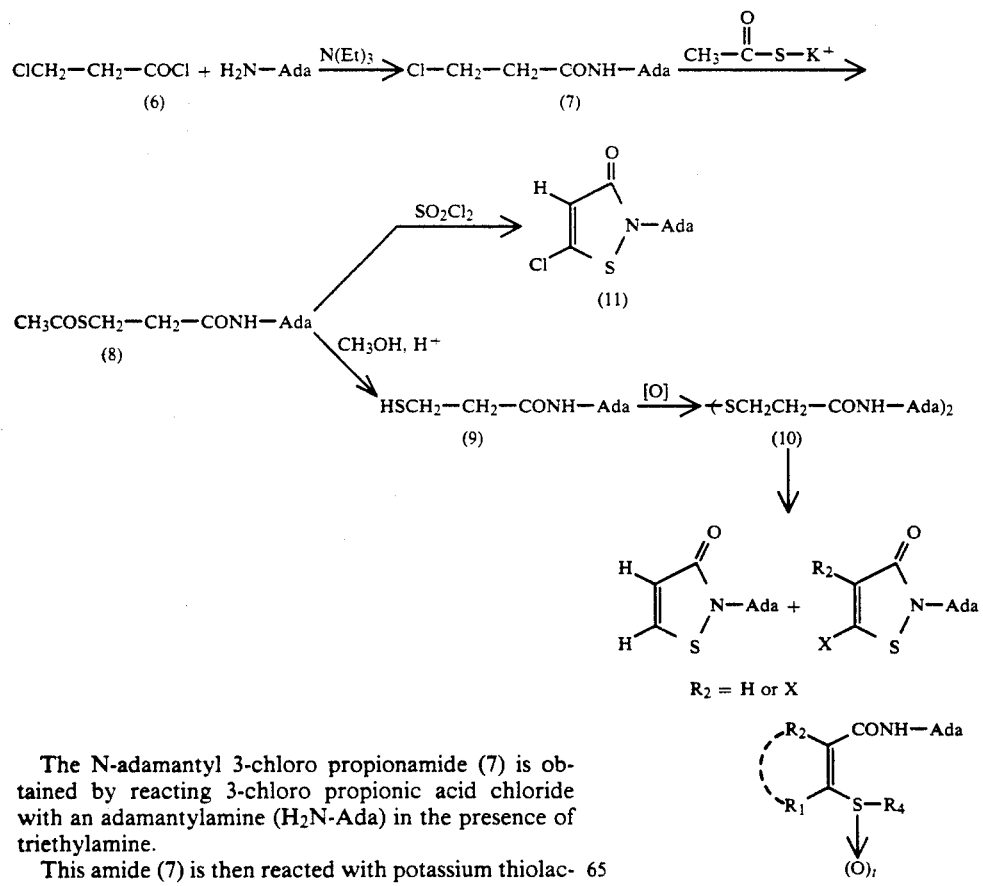

The N-adamantyl 3-chloro propionamide (7) is obtained by reacting 3-chloro propionic acid chloride with an adamantylamine ($H_2N$-Ada) in the presence of triethylamine.

This amide (7) is then reacted with potassium thiolacetate in an organic solvent such as acetone and leads, with a good yield, to N-adamantyl-3-acetylthio propionamide j(8). Starting with the latter, it is possible to wherein
t is 0 or 1, Ada has the same meaning as that given for formula (I), $R_1$ and $R_2$ have the same meanings as those given for formula (I) with the exclusion of $R_1$ and $R_2$, each independently, representing hydrogen or halogen, and $R_4$ represents alkyl or aralkyl.

As has been indicated previously, the 2-adamantyl-4-isothiazoline-3-ones, in accordance with the present invention, are particularly useful in destroying bacteria, fungus, molds, algae as well as all other parasites.

The invention thus also relates to a composition containing form 0.01 to 25 weight percent of at least one 2-adamantyl-4-isothiazoline-3-one, such as defined above, or an acid addition salt thereof as an active compound. The 2-adamantyl-4-isothiazoline-3-ones can be formulated as such or in the form of a complex with cyclodextrin in a solid, semi-solid or liquid vehicle.

Representative solid substances which can be employed as the vehicle appropriate for the preparation of a composition in the form of a powder, include various porous and pulverulent inert agents of an organic or inorganic nature such as tricalcium phosphate, calcium carbonate, kaolin, bentonite, talc, Kieselguhr, boric acid, powdered cork, sawdust and other fine pulverulent materials of a vegetable origin.

The active compound is mixed with the substances used as the vehicle, for example by being crushed with the vehicle. As a variation, the inert substance employed as the vehicle can be impregnated with a solution of the active compound in an easily volatilized solvent and the solvent is then removed by heating or filtration with aspiration under reduced pressure. By adding wetting and/or dispersing agents to the pulverulent preparations, which can be easily moistened with water, suspensions can be obtained.

The inert solvents employed for the preparation of liquid compositions must be non-inflammable and also odorless and non-toxic vis-a-vis warm blooded animals or plants.

It is also possible to use mixtures of solvents. Other liquid forms that can be employed include emulsions or suspensions, of an active compound according to the invention, in water or an appropriate inert solvent or also as a concentrate. To this end, the active compound is, for example, mixed with a dispersion or emulsifying agent. The active compound can also be dissolved or dispersed in an appropriate inert solvent and, simultaneously or subsequently, admixed with a dispersion or emulsifying agent. It is also possible to use semi-solid vehicles and in particular a creamy ointment or a paste in which the active compound is incorporated.

Moreover, it is also possible to use the active compounds of the present invention in the form of an aerosol. The active component is, in this case, dissolved or dispersed using an appropriate inert solvent. Solutions are obtained under pressure which, when they are atomized, give aerosols which are indeed particularly suitable to combat micro-organisms.

The compositions mentioned above can be applied by classic procedures such as by dusting, sprinkling, spraying, brushing, dipping, coating, impregnating, absorbing, injecting or any other appropriate manner.

The 2-adamantyl-4-isothiazoline-3-ones, in accordance with the present invention, or their salts can be employed in cosmetics as, for example, preservatives in compositions such as shampoos, capillary lotions, deodorants, sun products, and products for the face and body.

The 2-adamantyl-4-isothiazoline-3-ones can also be used as active compounds in cosmetic compositions provided in the form of solutions, dispersions, emulsions, creams, gels, pastes, aerosols, powders or soaps.

The present invention also relates to pharmaceutical compositions for human or veterinary medicine. These compositions can be provided in the form of solutions, emulsions, suspensions, creams, lotions, ointments, aerosols, powders, injectable solutions or suspensions, tablets, granules, gelules, capsules and can be administered according to the type of formulation, topically or any other general manner.

When the compounds according to the present invention are employed in cosmetic or pharmaceutical compositions, the concentration of the active compound is generally between 0.1 and 10 weight percent relative to the total weight of the composition.

In addition to their use in cosmetics and in human and veterinary pharmaceutical compositions, the compounds of the present invention are useful in other industrial fields such as agriculture, paper making, paints and enamels, water treatment and household maintenance products, principally clothes washing and disinfectant products.

When the compounds of the present invention are employed as anti-algae, antifungus and antibacteria agents in water treatment products, for example in swimming pools or water cooling systems, the requisite concentration is generally between 0.5 and 1,000 ppm.

When they are used in powdered or liquid laundry detergents, the concentration is preferably between 0.01 and 10 percent.

In antifouling and antifungus paints and enamels, the concentration of the active compound varies preferably between 0.1 and 25 g/liter.

There is now given as an illustration and without any limiting character, several examples of the preparation of 2-adamantyl-4-isothiazoline-3-ones according to the invention as well as several examples of their use. EXAMPLE I Preparation of
2-(1'-adamantyl)-4,5-trimethylene-4-isothiazoline-3-one (a) Preparation of 2-benzylthio cyclopentene N-(1'-adamantyl) carboxamide To a suspension, stirred under an inert atmosphere at ambient temperature, of 50 g of 2-benzylthio cyclopentene carboxylic acid in 300 cm$^3$ of dichloromethane, there are slowly added 13 cm$^3$ of phosphorus trichloride.

The mixture is then heated for three hours at the reflux of the solvent. At this stage the solution is homogeneous. It is then employed crude for the transformation into the amide.

To this solution, cooled at 0° C., there is slowly added a solution containing a mixture of 38.65 g of 1-adamantanamine (or anantadiene) and 75 cm$^3$ of triethylamine in 200 cm$^3$ of anhydrous methylene chloride. The addition completed, the reaction mixture is again stirred for two hours at ambient temperature, then it is poured into 1.5 liters of ice water. The organic phase is decanted, washed with an aqueous solution of 1N HC , then twice with water and finally dried on magnesium sulfate. The solvent is removed by evaporation under a vacuum and the resulting viscous liquid is poured into 300 cm$^3$ of isopropyl ether stirred at 0° C. The precipitate is filtered and dried, then recrystallized in 400 cm$^3$ of isopropyl ether. 54.7 g of 2-benzylthio cyclopentene N-(1'-adamantyl) carboxamide in the form of white crystals having a melting point of 91° C. are obtained.

| Elemental analysis: CH$_{29}$H$_{29}$NOS | | | | |
|---|---|---|---|---|
| Calculated: | C-75.16 | H-7.95 | N-3.81 | O-4.35 | S-8.72 |
| Found: | 74.60 | 8.04 | 3.79 | 4.92 | 8.62 |

(b) Preparation of 2-benzylsulfinyl cyclopentene N-(1'-adamantyl) carboxamide

To a suspension, stirred at 0° C., of 50 g of 2-benzylthio cyclopentene N-(1'-adamantyl) carboxamide in 300 cm$^3$ of formic acid, there are slowly added 14 cm$^3$ of H$_2$O$_2$ (30 vol). After the end of the addition, the reaction mixture is again stirred for two hours at ambient temperature, then poured directly into one liter of ice water. The sulfoxide is extracted with methylene chloride and the organic phase is washed with a 5% solution of sodium bicarbonate, then with water and finally dried on magnesium sulfate.

After evaporation of the solvent, 49 g of the sulfoxide are obtained which are washed with isopropyl ether. 48 g of 2-benzylsulfinyl cyclopentene N-(1'-adamantyl) carboxamide having a melting point of 148° C. are recovered.

| Elemental analysis: C$_{23}$H$_{29}$NO$_2$S | | | | |
|---|---|---|---|---|
| Calculated: | C-72.02 | H-7.62 | N-3.65 | O-8.34 | S-8.36 |
| Found: | 72.00 | 7.64 | 3.66 | 8.45 | 8.21 |

(c) Preparation of the hydrochloride of 2-(1'-adamantyl)-4,5-trimethylene-4-isothiazoline-3-one To a solution, stirred at 10° C., of 48 g of sulfoxide (obtained in step b) in 150 cm$^3$ of anhydrous methylene chloride there are slowly added 11 cm$^3$ of thionyl chloride. Stirring is then maintained for one hour at ambient temperature. Then, under vigorous stirring, there are rapidly added 200 cm$^3$ of isopropyl ether. The precipitate is filtered, dried and again stirred in 200 cm$^3$ of isopropyl ether thereby removing any trace of impurity. The crystals are filtered and dried and 27 g of white crystals having a melting point of 182° C. are obtained.

| Elemental analysis: C$_{16}$H$_{22}$ClNOS | | | |
|---|---|---|---|
| Calculated: | C-69.77 | H-7.69 | N-5.09 | S-11.64 |
| Found: | 69.54 | 7.77 | 4.94 | 11.30 |

EXAMPLE II

Preparation of 2-(1'-adamantyl methyl)-4,5-trimethylene-4-isothiazoline-3-one (a) Preparation of 2-benzylthio cyclopentene N-(1'-adamantyl methyl) carboxamide To a suspension, stirred under an inert atmosphere, of 4.7 g of 2-benzylthio cyclopentene carboxylic acid there are added 1.3 cm$^3$ of phosphorus trichloride. This mixture is then heated under reflux for 3 hours, at the end of which time the mixture is homogeneous. The solution is then cooled to 0° C. and there is slowly added a solution of 4 g of 1-adamantane methyl amine and 8.5 cm$^3$ of triethylamine in 25 cm$^3$ of methylene chloride.

The mixture is then stirred for one hour at ambient temperature and poured into 150 cm$^3$ of water. The organic phase is decanted, washed with an aqueous solution of 2N HCl, then twice with water and dried on magnesium sulfate. The methylene chloride is removed by evaporation under a vacuum and the resulting product is stirred in 40 cm$^3$ of isopropyl ether. The crystals are filtered and dried. 5.18 g of beige crystals having a melting point of 121° C. are obtained.

(b) Preparation of 2-benzylsulfinyl cyclopentene N-(1'-adamantyl methyl) carboxamide To a solution of 48 g of 2-benzylthio cyclopentene N-(1'-adamantyl methyl) carboxamide in 100 cm$^3$ of methylene chloride, stirred at 0° C. under an inert atmosphere in the absence of light, there are slowly added by small fractions, 2.3 g of metachloro perbenzoic acid. The mixture is then stirred for 2 hours at ambient temperature, washed with a saturated solution of sodium bicarbonate, then with water, dried on magnesium sulfate and concentrated.

The resulting concentrated solution is poured into 50 cm$^3$ of isopropyl ether stirred at 0° C. The resulting precipitate is filtered, then dried and 2.85 g of 2-benzylthio cyclopentene N-(1'adamantyl methyl) carboxamide in the form of beige crystals having a melting point of 168° C. are obtained.

This product is analyzed under hydrated form.

| Elemental analysis: CH$_{24}$H$_{31}$NO$_2$S - ½ H$_2$O | | | |
|---|---|---|---|
| Calculated: | C-70.89 | H-7.93 | N-3.44 | S-7.88 |
| Found: | 70.69 | 7.92 | 3.44 | 7.62 |

(c) Preparation of the hydrochloride of 2-(1'-adamantyl methyl)-4,5-trimethylene-4-isothiazoline-3-one To a suspension, stirred under an inert atmosphere at 0° C., of 2.6 g of 2-benzylsulfinyl cyclopentane N-(1'-adamantyl methyl) carboxamide in 25 cm$^3$ methylene chloride there is slowly added 0.6 cm$^3$ of thionyl chloride. The mixture is then stirred for 1 hour at ambient temperature, and poured into 200 cm$^3$ of isopropyl ether stirred at −10° C.

The precipitated product is filtered, dissolved in a minimum of methylene chloride and precipitated by the addition of pentane. The crystals are filtered and dried. 1.60 g of the hydrochloride of 2-(1'-adamantyl methyl)-4,5-trimethylene-4-isothiazoline-3-one in the form of white crystals having a melting point of 161° C. are obtained.

| Elemental analysis: C$_{17}$H$_{24}$ClNOS | | | | |
|---|---|---|---|---|
| Calculated: | C-62.65 | H-7.42 | C-10.88 | N-4.30 | S-9.84 |
| Found: | 62.68 | 7.78 | 10.71 | 4.40 | 9.66 |

(d) Preparation of 2-(1'-adamantyl methyl)-4,5-trimethylene-4-isothiazoline-3-one A solution of 1.50 g of the hydrochloride (prepared according to step c) in 100 cm$^3$ of methylene chloride is washed three times with 50 cm$^3$ of water. The hydrochloride is completely removed. The methylene chloride phase is decanted, dried on sodium sulfate and concentrated.

This concentrated solution is poured into iced hexane. The crystallized product is filtered and dried. 1.20 g of 2-(1'-adamantyl methyl)-4,5-trimethylene-4-isothiazoline-3-one in the form of white crystals having a melting point of 145° C. are obtained.

| Elemental analysis: $C_{17}H_{23}NOS$ | | | | | |
|---|---|---|---|---|---|
| Calculated: | C-70.54 | H-8.01 | N-4.84 | O-5.53 | S-11.08 |
| Found: | 70.52 | 7.79 | 4.82 | 5.70 | 10.95 |

Example III

Preparation of 2-(2'-adamantyl)-4,5-trimethylene-4-isothiazoline-3-one

Preparation of 2-benzyl thio cyclopentene N-(2'-adamantyl) carboxamide

To a solution, stirred at ambient temperature under an inert atmosphere, of 25.2 g of 2-benzylthio cyclopentene carboxylic acid in 200 cm³ of dichloromethane there are slowly added 9.3 cm³ of phosphorus trichloride. The addition is not exothermic and the mixture is then brought to reflux for 2 hours, and left overnight at ambient temperature.

The next day this solution of crude acid chloride is added directly, and slowly, to a mixture of 19.5 g of 2-adamantanamine and 45.1 cm³ of triethylamine in 200 cm³ of anhydrous methylene chloride cooled to 0° C.

The reaction is strongly exothermic. The addition completed, the mixture is stirred for 2 hours at ambient temperature, and poured into 50 cm³ of water. The organic phase is decanted, washed with an aqueous solution of 2N HCl, then with water until the wash waters have a neutral pH and finally dried on magnesium sulfate. After evaporation under a vacuum of the methylene chloride 28.8 g of crude 2-benzyl thiocyclopentene N-(2'-adamantyl) carboxamide are obtained which is used as such for the following step.

(b) Preparation of 2-benzylsulfinyl cyclopentene N-(2'-adamantyl) carboxamide

To a solution, stirred under an inert atmosphere at 0° C., of 29 g of 2-benzylthio cyclopentene N-(2'-adamantyl) carboxamide in 200 cm³ of formic acid, there are slowly added 8.1 cm³ of $H_2O_2$ (110 vol). The addition completed, the reaction mixture is again stirred for 2 hours at ambient temperature, and concentrated under reduced pressure. The resulting product is dissolved in 300 cm³ of methylene chloride. The organic solution is then washed with a 2N aqueous solution of soda until the wash waters have a neutral pH and finally dried on magnesium sulfate.

After evaporation of the methylene chloride, the resulting crystals are stirred in a pentane-isopropyl ether mixture, then filtered and dried.

The 31 g of the resulting crude product are dissolved in a minimum of methylene chloride and the solution is introduced into a silica gel chromatography column that is eluted initially with methylene chloride and then with a methylene chloride-ethyl acetate mixture progressively enriched in ethyl acetate. After evaporation of the solvent from fractions containing the pure product, 15 g of 2-benzylsulfinyl cyclopentene N-(2'-adamantyl) carboxamide in the form of white crystals having a melting point of 185° C. are obtained.

| Elemental analysis: $C_{23}H_{29}NO_2S$ | | | | | |
|---|---|---|---|---|---|
| Calculated: | C-72.02 | H-7.62 | N-3.65 | O-8.34 | S-8.36 |
| Found: | 71.81 | 7.69 | 3.68 | 8.09 | 8.24 |

(c) Preparation of the hydrochloride of 2-(2'-adamantyl)-4,5-trimethylene-4-isothiazoline-3-one.

To a solution, stirred under an inert atmosphere at 0° C., of 13 g of 2-benzylsufinyl cyclopentene N-(2'-adamantyl) carboxamide in 100 cm³ of dichloromethane there are slowly added 13 g of thionyl chloride. The reaction is slightly exothermic. The addition completed, the mixture is again stirred for 1 hour at ambient temperature.

It is then poured into 200 cm³ of isopropyl ether stirred at 0° C. The precipitate is filtered and dried. 8 q of the hydrochloride of 2-(2'-adamantyl)-4,5-trimethylene-4-isothiazoline-3-one in the form of beige crystals having a melting point of 175° C. are obtained.

| Elemental analysis: $C_{16}H_{21}ClNOS$ | | | | | |
|---|---|---|---|---|---|
| Calculated: | C-61.61 | H-7.11 | Cl-11.37 | H-4.49 | S-10.25 |
| Found: | 61.39 | 7.40 | 11.26 | 4.42 | 10.18 |

(d) Preparation of 2-(2'-adamantyl)-4,5-trimethylene-4-isothiazoline-3-one.

A solution of 7.5 g of the hydrochloride of 2-(2'-adamantyl)-4,5-trimethylene-4-isothiazoline-3-one in 150 cm³ of methylene chloride is washed three times with water. At the third washing, the hydrochloride is completely removed. The methylene chloride phase is dried on magnesium sulfate and then concentrated. To this concentrated solution, stirred at 0° C., pentane is added. The precipitate is filtered and dried. 5.2 g of 2-(2'-adamantyl)-4,5-trimethylene-4-isothiazoline-3-one in the form of beige crystals having a melting point of 140° C. are obtained.

| Elemental analysis: $C_{16}H_{21}NOS$ | | | | | |
|---|---|---|---|---|---|
| Calculated: | C-69.77 | H-7.69 | N-5.09 | O-5.81 | S-11.64 |
| Found: | 69.64 | 7.72 | 5.13 | 6.07 | 11.61 |

EXAMPLE IV

Preparation of 2-(2'adamantyl)-(5,4b)-isothiazolo-3-pyridinone (a) Preparation of N-(2'-adamantyl)-2-chloro nicotinamide (i) Preparation of the acid chloride of 2-chloronicotinic acid A suspension of 20 g of 2-chloronicotinic acid in 100 cm³ of thionyl chloride is brought, with stirring, to reflux for 2 hours. At this stage, the reaction mixture is homogeneous. The unreacted thionyl chloride is evaporated under reduced pressure yielding the acid chloride in the form of white nacreous flakes that are dissolved in 50 cm³ of anhydrous dichloromethane.

(ii) Preparation of the amide

This solution of the acid chloride is slowly added to a mixture, vigorously stirred under an inert atmosphere at 0° C., of 23 g of 2-adamantanamine and 89 cm³ of triethylamine in 250 cm³ of anhydrous methylene chloride. The addition of the acid chloride completed, the resulting heterogeneous mixture is again stirred for 2 hours at ambient temperature. It is then poured into 400 cm³ of water and the organic phase is decanted, washed with a normal solution of NC and then with water. The organic phase is dried on magnesium sulfate, and concentrated under reduced pressure. The resulting beige solid is dissolved in 100 cm³ of anhydrous methylene chloride. After cooling, the resulting crystals are filtered and dried. 25 g of N-(2'-adamantyl)-2-chloro nicotinamide whose NMR H[1] spectrum corresponds to the expected structure are obtained.

(b) Preparation of N-(2'-adamantyl)-2-benzylthio nicotinamide

In a first stage potassium benzylthiolate is prepared by dissolving 12.3 cm³ of benzylmercaptan in 300 cm³ of 2-ethoxyethanol to which have been added 6.9 g of potash pellets. To this solution, stirred under an inert atmosphere at ambient temperature, there are added, by portions, 25 g of N-(2'-adamantyl)-2-chloronicotinamide. The mixture is again stirred for 3 hours and an insoluble progressively appears.

The next day this latter is filtered and dissolved in 300 cm³ of dichloromethane. The resulting solution is washed three times with 200 cm³ of water and the organic phase is dried on magnesium sulfate.

The solvent is removed by evaporation under a vacuum and the resulting solid is stirred in 100 cm³ of isopropyl ether so as to entirely finely divide it.

It is filtered and dried. 26 g of N-(2'-adamantyl)-2-benzylthio nicotinamide in the form of white nacreous flakes having a melting point of 170° C. are obtained.

| Elemental analysis: C₂₃H₂₆N₂OS | | | | |
|---|---|---|---|---|
| Calculated: | C-72.98 | H-6.92 | N-7.40 | O-4.23 | S-8.47 |
| Found: | 72.77 | 7.01 | 7.28 | 4.38 | 8.28 |

(c) Preparation of N-(2'-adamantyl)-2-benzylsulfinyl nicotinamide

To a solution, stirred under an inert atmosphere at 0° C., of 25 g of N-(2'-adamantyl)-2-benzylthio nicotinamide in 200 cm³ of formic acid there are added 7.5 cm³ of H₂O₂ (110 vol).

The solution is then stirred for 3 hours at ambient temperature.

The formic acid is removed by evaporation under a vacuum and the resulting product is dissolved in 300 cm³ of dichloromethane. This solution is washed with a normal solution of soda and then with water.

The organic phase is decanted, dried on magnesium sulfate and the solvent is removed by evaporation under reduced pressure. A solid is obtained which is washed with isopropyl ether and dried. The 22 g of N-(2'-adamantyl)-2-benzylsulfinyl nicotinamide thus isolated have a melting point of 218° C.

| Elemental analysis: C₂₃H₂₆N₂O₂S | | | | |
|---|---|---|---|---|
| Calculated: | C-70.02 | H-6.64 | N-7.10 | O-8.11 | S-8.13 |
| Found: | 69.97 | 6.66 | 6.97 | 8.21 | 7.94 |

(d) Preparation of the hydrochloride of 2-(2'-adamantyl)-(5,4b)-isothiazolo-3-pyridinone To a solution, stirred at 0° C. under an inert atmosphere of 21 g of N-(2'-adamantyl)-2-benzylsulfinyl nicotinamide in 100 cm³ of methylene chloride there are slowly added 4.6 cm³ of thionyl chloride. A product precipitates and the mixture is again stirred for 1 hour at ambient temperature. The precipitate is filtered, washed with isopropyl ether, then with pentane and finally dried.

15 g of the hydrochloride of 2-(2'-adamantyl)-(5,4b)-isothiazolo-3-pyridinone in the form of yellow crystals having a melting point of 188° C. are obtained.

| Elemental analysis: C₁₆H₁₉ClN₂OS | | | | | |
|---|---|---|---|---|---|
| Calculated: | C-59.72 | H-5.93 | Cl-10.98 | N-8.68 | O-4.96 | S-9.93 |
| Found: | 59.53 | 5.94 | 10.89 | 8.75 | 5.22 | 9.86 |

(e) Preparation of 2-(2'-adamantyl)-(5,4b)-isothiazolo-3-pyridinone

A solution of 13 g of the preceding hydrochloride in 500 cm³ of methylene chloride is stirred in the presence of 200 cm³ of an aqueous soda solution.

The organic phase is decanted, washed again three times with pure water and then dried on magnesium sulfate. The methylene chloride is removed by evaporation under a vacuum and the resulting solid is vigorously stirred in 100 cm³ of pentane, filtered and dried. 10.5 g of 2-(2'-adamantyl)-(5,4b)-isothiazolo-3-pyridinone in the form of white crystals having a melting point of 108° C. are obtained.

| Elemental analysis: C₁₆H₁₈N₂OS | | | | |
|---|---|---|---|---|
| Calculated: | C-67.10 | H-6.33 | N-9.78 | O-5.59 | S-11.20 |
| Found: | 66.89 | 6.32 | 9.88 | 5.75 | 11.07 |

Preparation of the synthesis intermediates of 2-(2'-adamantyl)-4-isothiazoline-3-one and its halogenated (chlorinated) homologs in position 4 or positions 4 and 5

A. Preparation of N-(2'-adamantyl)-3-chloro propionamide

To a solution, stirred at 0° C. under an inert atmosphere, of 106 g of 3-chloro propionic acid chloride in 400 cm³ of 1,2-dichloroethane there is slowly introduced a mixture containing 120 g of 2-adamantanamine and 80.32 g of triethylamine dissolved in 1 liter of 1,2-dichloroethane.

The reaction is exothermic and the rate of introduction is regulated in such a manner that the temperature does not exceed 5° C.. After the end of the introduction the mixture is again stirred for 1 hour 30 minutes.

At this stage, the majority of the starting product is transformed and there are then introduced 500 cm³ of 3N HCl with stirring. The organic phase is then decanted, washed three times with water, dried on sodium sulfate and concentrated. The resulting crude product is recrystallized in a mixture of 1 liter of isopropyl ether and 350 cm³ of ethyl acetate.

150 g of N-(2'-adamantyl)-3-chloro propionamide in the form of white crystals whose melting point is 125°–126° C. are obtained.

The NMR¹H spectrum conforms to the expected structure.

B. Preparation of 3-acetylthio N-(2'-adamantyl) propionamide

To a solution, stirred at ambient temperature under an inert atmosphere, of 147 of N-(2'-adamantyl)-3-chloro propionamide in 1.5 liters of anhydrous acetone there are added, in small fractions, 69.32 g of potassium thiolacetate. The mixture is then progressively brought to the reflux of the solvent. Four hours later all of the initial reactant is transformed.

The acetone is then evaporated under reduced pressure and the resulting solid is dissolved in dichloromethane. The resulting solution is washed three time with water, then dried on sodium sulfate and concentrated.

165 g of solid that is obtained are dissolved in a boiling 1:1 isopropyl ether-toluene mixture in the presence of animal black.

The boiling solution is filtered and then cooled. The crystallized 3-acetylthio N-(2'-adamantyl) propionamide is filtered and dried. 140 g of product in the form of beige crystals whose melting point is 124° C. are recovered.

| Elemental analysis: $C_{15}H_{23}NO_2S$ | | | | | |
|---|---|---|---|---|---|
| Calculated: | C-64.02 | H-8.23 | N-4.97 | O-11.37 | S-11.39 |
| Found: | 64.47 | 8.29 | 4.89 | 11.58 | 11.09 |

C. Preparation of N-(2'-adamantyl)-3-mercapto propionamide

A solution, stirred under an inert atmosphere, of 46 g of 3-acetylthio N-(2'-adamantyl) propionamide in a mixture of 1 liter of methanol and 50 cm³ of 2N HCl is brought to the reflux of the solvent for 6 hours. The solvent is then removed under reduced pressure and the resulting solid is dissolved in methylene chloride.

The solution is then washed several times with water, dried on sodium sulfate and concentrated. 43 g of N-(2'-adamantyl)-3-mercapto propionamide in the form of a white powder whose NMR¹H spectrum conforms to the structure are obtained.

D. Preparation of the disulfide of N-(2'-adamantyl)-3-mercapto propionamide

A solution of 25.92 g of N-(2'-adamantyl)-3-mercapto propionamide in 500 cm³ of methanol is stirred at a temperature between 0° and 5° C. There are slowly added 20 cm³ of concentrated ammonia and then 10 cm³ of $H_2O_2$(110 vol). The mixture is stirred at ambient temperature until all of the initial reactant is transformed. The disulfide crystallizes in the reaction mixture and after cooling, the solid is filtered, then dried and recrystallized in methanol. 30 g of the disulfide of N-(2'-adamantyl)-3-mercapto propionamide in the form of white crystals having a melting point of 199° C. are obtained.

| Elemental analysis: $C_{26}H_{40}N_2O_2S_2$ | | | | | |
|---|---|---|---|---|---|
| Calculated: | C-65.50 | H-8.45 | N-5.87 | O-6.71 | S-13.45 |
| Found: | 65.38 | 8.41 | 5.90 | 6.86 | 13.45 |

E. Preparation of N-(1'-adamantyl)-3-chloro propionamide

To a solution, stirred at a temperature of about −10° C., of 29 g of 3-chloro propionic acid chloride in 400 cm³ of 1,2-dichloroethane there is slowly introduced a solution containing 68.5 g of 1-adamantamine (2 equivalents) in 600 cm³ of 1,2-dichloroethane. The reaction is exothermic and the rate of introduction is regulated in a manner so as to maintain the temperature between −8° and −12° C.

At the end of the introduction the temperature is permitted to return towards 0° C., the temperature at which the white precipitate of 1-adamantamine hydrochloride is filtered. The filtrate is washed with 0.1N HCl, then with water dried on sodium sulfate. After removal of the solvent, the crude amide is recrystallized in isopropyl ether. 45 g of N-(1'-adamantyl)-3-chloro propionamide in the form of white crystals having a melting point of 121° C. are obtained.

| Elemental analysis: $C_{13}H_{20}ClNO$ | | | | | |
|---|---|---|---|---|---|
| Calculated: | C-64.58 | H-8.34 | Cl-14.67 | N-5.79 | O-6.62 |
| Found: | 64.18 | 8.40 | 15.23 | 5.82 | 6.66 |

F. Preparation of 3-acetylthio N-(1'-adamantyl) propionamide

To a solution, stirred at ambient temperature under inert atmosphere, of 42.4 g of N-(1'-adamantyl)-3-chloro propionamide in 600 cm³ of anhydrous acetone there are added in small fractions 20 g of potassium thiolacetate. The mixture is then progressively brought to the reflux of the solvent. Six hours later the majority of the initial reactant is transformed and the acetone is then evaporated. The product is dissolved in a mixture of methylene chloride and water and the organic phase is decanted, washed three times with water, dried on sodium sulfate and then concentrated.

After recrystallization of the resulting crude product in isopropyl ether 42 g of 3-acetylthio N-(1'-adamantyl) propionamide in the form of white crystals having a melting point of 104° C. are obtained.

| Elemental analysis: $C_{15}H_{23}NO_2S$ | | | | | |
|---|---|---|---|---|---|
| Calculated: | C-64.02 | H-8.24 | N-4.98 | O-11.37 | S-11.39 |
| Found: | 63.73 | 8.24 | 5.09 | 11.56 | 11.63 |

EXAMPLE V

Preparation of 2-(2'-adamantyl)-4-isothiazolo-3-one

A solution of 18.4 of chlorine in 800 cm³ of anhydrous ethyl acetate is prepared. To this solution there are added with stirring, at ambient temperature, 40 g of 3-acetylthio N-(2'-adamantyl) propionamide in solid form. The temperature rises to 34° C. and the mixture becomes homogeneous. One-half hour later an insoluble forms.

Stirring is continued for three additional hours. The precipitate is then filtered and dried. 15.20 of crude 2-(2'-adamantyl)-4-isothiazoline-3-one in hydrochloride form are obtained which is then dissolved in 300 cm³ of methylene chloride. The resulting solution is washed three times with water, dried on sodium sulfate and evaporated under reduced pressure.

The resulting solid containing impurities is extracted several times with boiling hexane and the hexane solutions are then concentrated until the onset of crystallization is observed.

The mixture is then cooled and the crystals are filtered and dried. 10 g of 2-(2'-adamantyl)-4-isothiazoline-3-one in the form of white crystals having a melting point of 153° C. are obtained.

| Elemental analysis: $C_{13}H_{17}NOS$ | | | | |
|---|---|---|---|---|
| Calculated: C-66.34 | H-7.28 | N-5.95 | O-6.80 | S-13.62 |
| Found: 66.40 | 7.26 | 5.93 | 7.03 | 13.54 |

Example VI

Preparation of 2-(2'-adamantyl)-5-chloro-4-isothiazoline-3-one

A solution, stirred in the absence of light, of 87 g of sulfuryl chloride, in 1.4 liters of anhydrous toluene is cooled to a temperature between −15° and −10° C. There are then rapidly added 60 g of 3-acetylthio N-(2'-adamantyl) propionamide in solid form. For a few minutes the reaction mixture is homogeneous but then an insoluble rapidly appears. One-half hour after the end of the addition the temperature of the mixture is left to return to ambient temperature (20° C.). At this stage the mixture is homogeneous. Stirring is again continued for three hours at ambient temperature. There are then added one liter of water and finally sodium bicarbonate to adjust the pH of the aqueous phase to about 5.5. The organic phase is then decanted, washed with water, dried on sodium sulfate and finally concentrated under reduced pressure. 62.5 g of a crude product in the form of a viscous liquid are obtained which is then chromatographed by passage through a silica gel chromatography column. The expected product is eluted with methylene chloride and then with a methylene chloride-ethyl acetate mixture. After removal of the solvent under reduced pressure 40 g of 2-(2'-adamantyl)-5-chloro-4-isothiazoline-3-one are obtained.

After recrystallization in ethyl acetate 25 g of white crystal having a melting point of 111° C. are recovered.

| Elemental analysis: $C_{13}H_{16}ClNOS$ | | | | | |
|---|---|---|---|---|---|
| Calculated: C-57.87 | H-5.97 | Cl-13.14 | N-5.19 | O-5.93 | S-11.88 |
| Found: 57.97 | 5.97 | 13.30 | 5.17 | 6.07 | 11.77 |

Example VII

Preparation of 2-(2'-adamantyl)-4,5-dichloro-4-isothiazoline-3-one

Into a solution of 15 g of the disulfide of N-(2'-adamantyl)-3-mercaptopropionamide in 500 cm³ of 1,2-dichloroethone there is slowly introduced a stream of chlorine in a manner so as to capture about 25 g in about three hours. The temperature of the stirred solution is maintained during this time at 20° C.

Then a strong stream of gaseous nitrogen is passed through the solution to remove unreacted chlorine as well as HC gas. There are then added about 300 cm³ of water with stirring and the pH of the aqueous phase is adjusted to about 5.5 by the addition of sodium bicarbonate. The organic phase is decanted, washed with water, dried on sodium sulfate and concentrated.

This concentrated solution is introduced into a silica gel chromatography column and is eluted with methylene chloride and then with a methylene chloride-ethanol mixture in a manner so as to obtain fractions enriched in the dichloro derivative. These different enriched fractions are evaporated under a vacuum. The resulting product is then dissolved in toluene and again introduced into a silica gel chromatography column and eluted this time with toluene progressively enriched with methylene chloride and then with a methylene chloride-ethyl acetate mixture. The fractions containing the dichloro derivative are combined and evaporated under a vacuum. The resulting solid is recrystallized in a minimum of ethyl acetate. 3 g of 2-(2'-adamantyl)-4,5-dichloro-4-isothiazoline-3-one in the form of beige needles having a melting point of 142° C. are obtained.

| Elemental analysis: $C_{13}H_{15}Cl_2NOS$ | | | | |
|---|---|---|---|---|
| Calculated: C-51.32 | H-4.96 | N-4.60 | O-5.25 | S-10.53 |
| Found: 51.38 | 4.97 | 4.72 | 5.45 | 10.40 |

Example VIII

Preparation of 2-(1'-adamantyl)-4-isothiazoline-3-one

To a solution, stirred at ambient temperature, of 10 g of 3-acetylthio N-(1'-adamantyl) propionamide in 250 cm³ of anhydrous methylene chloride there are slowly added 7.2 g of sulfuryl chloride (1.5 equivalents) diluted in 60 cm³ of methylene chloride. Two hours after the end of the introduction, there is slowly added with stirring, while maintaining the temperature lower than 20° C., a solution of sodium bicarbonate until the pH of the aqueous phase is about 6. The organic phase is then decanted, washed with water, dried on sodium sulfate, concentrated and finally introduced into a silica gel chromatography column that is eluted with methylene chloride.

After evaporation of the solutions containing the anticipated product and recrystallization in acetone, 4 g of 2-(1'-adamantyl)-4-isothiazoline-3-one in the form of white crystals having a melting point of 169° C. are obtained.

| Elemental analysis: $C_{13}H_{17}OS$ | | | | |
|---|---|---|---|---|
| Calculated: C-66.34 | H-7.28 | N-5.95 | O-6.80 | S-13.62 |
| Found: 66.27 | 7.32 | 5.96 | 7.04 | 13.74 |

Example IX

Preparation of 2-(1'-adamantyl)-5-chloro-4-isothiazoline-3-one and 2-(1'-adamantyl)-4,5-dichloro-4-isothiazoline-3-one To a solution, stirred at ambient temperature and under an inert atmosphere, of 10 g of 3-acetylthio N-(1'-adamantyl) propionamide in 200 cm³ of anhydrous toluene there are slowly added 10 cm³ of sulfuryl chloride (3.5 equivalents) in a manner such that the temperature does not exceed 24° C. The precipitate which forms at the beginning of the introduction dissolves progressively. Three hours after the end of the introduction there are added 200 cm³ of water and then, with stirring, there is slowly introduced a solution of sodium bicarbonate so as to adjust the pH of the aqueous phase to about 6. The organic phase is then decanted, washed several times with water, dried on sodium sulfate and the solvent is removed by evaporation under a vacuum. The 8.5 g of resulting crude product, dissolved in a minimum of methylene chloride, are introduced into a silica gel chromatography column and eluted with methylene chloride and then with a methylene chloride-ethyl acetate mixture progressively enriched in ethyl acetate.

After evaporation of the solutions containing the purified products there are recovered, at the head of chromatography, 6.2 g of 2-(1'-adamantyl)-5-chloro-4-isothiazoline- 3-one. After recrystallization in a minimum of ethyl acetate, 3.6 g of white crystals having a melting point of 121° C. are obtained.

| Elemental analysis: $C_{13}H_{16}ClNOS$ | | | | | |
|---|---|---|---|---|---|
| Calculated: | C-57.87 | H-5.97 | Cl-13.14 | N-5.19 | O-5.93 S-11.88 |
| Found: | 57.91 | 6.00 | 13.21 | 5.09 | 6.01 11.67 |

In the mixtures more rich in ethyl acetate the dichloro derivative is entrained and isolated after evaporation of the eluant and then recrystallized in ethyl acetate. 0.5 g of 2-(1'-adamantyl)-4,5-dichloro-4-isothiazoline-3-one in the form of beige crystals having a melting point of 202° C. is obtained.

| Elemental analysis: $C_{13}H_{15}Cl_2NOS$ | | | | | |
|---|---|---|---|---|---|
| Calculated: | C-51.32 | H-4.96 | Cl-23.30 | N-4.60 | O-5.25 S-10.53 |
| Found: | 51.43 | 4.98 | 23.08 | 4.52 | 5.40 10.38 |

| Example of Compositions | |
|---|---|
| Example A - Nonionic cream | |
| 2-(2'-adamantyl)-(5,4b)-isothiazolo-3-pyridinone | 1.00 g |
| Sorbitan monostearate polyoxyethylenated with 20 moles of ethylene oxide | 3.50 g |
| Sorbitan monostearate | 1.50 g |
| Glycerol monostearate | 14.00 g |
| Cetyl alcohol | 0.50 g |
| 2-octyl dodecanol | 3.00 g |
| Decylester of oleic acid | 6.00 g |
| Twice distilled glycerol | 5.00 g |
| Sterile demineralized water | 65.50 g |
| Example B - Hydroethanolic gel | |
| 2-(1'-adamantyl)-4,5-trimethylene-4-isothiazoline-3-one | 0.10 g |
| Ethanol | 30.00 g |
| Propylene glycol | 30.00 g |
| Hydroxypropyl cellulose | 2.00 g |
| Demineralized water | 37.90 g |
| Example C - Cream soap | |
| 2-(2'-adamantyl)-4-isothiazoline-3-one | 5.00 g |
| Mixture of sodium lauryl ether sulfate and coco diethanolamide with 35% active material | 87.00 g |
| Coco dimethylamidobetaine | 8.00 g |
| Example D - 0.5 g tablet for oral administration | |
| 2-(2'-adamantyl)-4-isothiazoline-3-one | 0.250 g |
| Starch | 0.038 g |
| Dicalcium phosphate | 0.100 g |
| Lactose | 0.075 g |
| Talc | 0.025 g |
| Magnesium stearate | 0.012 g |

In this example, the active compound can be replaced by 2-(2'-adamantyl)-(5,4b)-isothiazolo-3-pyridinone.

| Example E - 2 g effervescent tablet | |
|---|---|
| 2-(2'-adamantyl)-5-chloro-4-isothiazoline-3-one | 0.250 g |
| Finely pulverized sucrose | 1.545 g |
| Sodium bicarbonate | 0.065 g |
| Granulated citric acid | 0.110 g |
| Gum arabic | 0.015 g |
| Stearic acid | 0.005 g |
| Powdered flavoring | 0.010 g |

In this example, the active compound can be replaced by 2-(1'-adamantyl)-4,5-trimethylene-4-isothiazoline-3-one.

| Example F - Powder for gelule | |
|---|---|
| 2-(2'-adamantyl)-4,5-dichloro-4-isothiazoline-3-one | 0.10 g |
| Starch | 0.06 g |
| Magnesium stearate | 0.01 g |
| Sucrose | 0.26 g |

This powder is packaged in standard gelules.
The following compounds:
2-(2'-adamantyl)-4-isothiazoline-3-one,
2-(2'-adamantyl)-5-chloro-4-isothiazoline-3-one, and
2-(2'-adamantyl)-4,5-dichloro-4-isothiazoline-3-one,
are shown to be particularly useful as anti-algae, antifungus and antibacteria agents in the treatment of water, in liquid or powder detergents and in industrial paints and enamels.

What is claimed is:

1. 2-adamantyl-4-isothiazolone-3-one having the formula

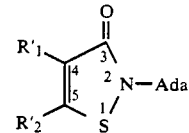

wherein
Ada represents an adamantyl radical selected from the group consisting of

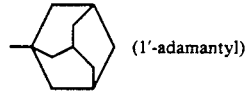

(i) (1'-adamantyl)

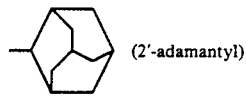

(ii) (2'-adamantyl)

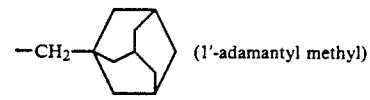

(iii) (1'-adamantyl methyl)

$R'_1$ and $R'_2$, each independently, represent hydrogen or halogen, and
the mineral or organic acid salt thereof.

2. The compound of claim 1 wherein said halogen is fluorine, bromine or chlorine.

3. The compound of claim 1 in the form of its hydrochloride, hydrobromide, nitrate, sulfate or succinate.

4. The compound of claim 1 selected from the group consisting of
2-(2'-adamantyl)-4-isothiazoline-3-one,
2-(2'-adamantyl)-5-chloro-4-isothiazoline-3-one,
2-(2'-adamantyl)-4,5-dichloro-4-isothiazoline-3-one,
2-(1'-adamantyl)-4-isothiazoline-3-one,
2-(1'-adamantyl)-5-chloro-4-isothiazoline-3-one,
2-(1'-adjamantyl)-4,5-dichloro-4-isothiazoline-3-one,
2-(1'-adamantyl)-5-bromo-4-isothiazoline-3-one,
2-(1'-adamantyl)-4-bromo-5-chloro-4-isothiazoline-3-one and
2-(2'-adamantyl)-4-bromo-5-chloro-4-isothiazoline-3-one.

5. A pharmaceutical composition for human or veterinary use comprising in a pharmaceutically acceptable medium at least one compound of claim 1.

6. The pharmaceutical composition of claim 5 wherein said compound is present in an amount ranging from 0.1 to 10 weight percent.

7. 2-adamantyl-4-isothiazolone-3-one having the formula

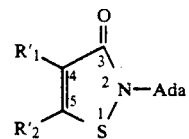

wherein
Ada represents 1'-adamantyl or 2'-adamantyl and $R'_1$ and $R'_2$ represent hydrogen or chlorine with at least one of $R'_1$ and $R'_2$ representing chlorine.

8. The compound of claim 7 wherein Ada represents 2-adamantyl.

* * * * *